United States Patent [19]
Strojnik

[11] Patent Number: 5,640,764
[45] Date of Patent: Jun. 24, 1997

[54] METHOD OF FORMING A TUBULAR FEED-THROUGH HERMETIC SEAL FOR AN IMPLANTABLE MEDICAL DEVICE

[75] Inventor: Primoz Strojnik, Granada Hills, Calif.

[73] Assignee: Alfred E. Mann Foundation for Scientific Research, Sylmar, Calif.

[21] Appl. No.: 446,138

[22] Filed: May 22, 1995

[51] Int. Cl.$^6$ ............................................. H01R 43/00
[52] U.S. Cl. ................................... 29/856; 174/52.3
[58] Field of Search ........................... 29/593, 855, 856, 29/50.5; 174/52.1–52.4, 50.64; 65/43

[56] References Cited

U.S. PATENT DOCUMENTS

| | | | |
|---|---|---|---|
| 4,152,540 | 5/1979 | Duncan et al. | 174/152 |
| 4,850,227 | 7/1989 | Luettgen et al. | 29/621.1 |
| 4,991,582 | 2/1991 | Byers et al. | 128/419 |
| 5,312,439 | 5/1994 | Loeb | 607/2 |
| 5,405,367 | 4/1995 | Schulman et al. | 607/61 |

*Primary Examiner*—P. W. Echols
*Assistant Examiner*—Adrian L. Coley
*Attorney, Agent, or Firm*—Fitch, Even, Tabin & Flannery

[57] ABSTRACT

A method and apparatus for hermetically sealing implantable devices, such as a microstimulator, moicrotransducer, microtelemeter, or the like, prevents entrapment of water vapors and other volatile gases, and allows hermeticity testing at all manufacturing levels. The venting of water vapors and other volatile gases is accomplished with a tubular feedthrough that allows such gases trapped within the sealed device to vent during the manufacturing process. The tubular feedthrough also establishes a conduit through which leakage tests or other hermeticity tests can be conducted prior to and after sealing the feedthrough. The tubular feedthrough, when made from conductive materials, also provides for electrical connections between electronic circuits sealed within the device and electrodes and other electrical terminals on the outside of the capsule.

13 Claims, 2 Drawing Sheets

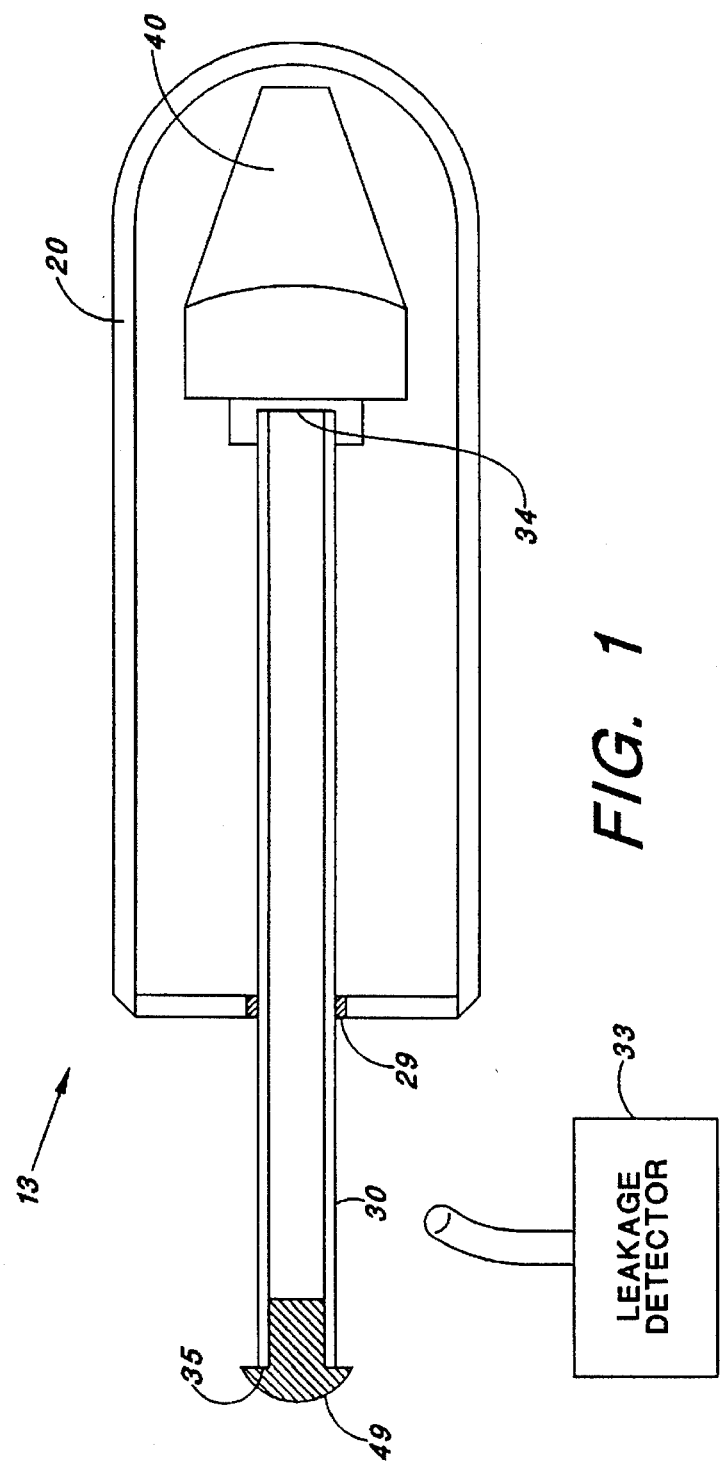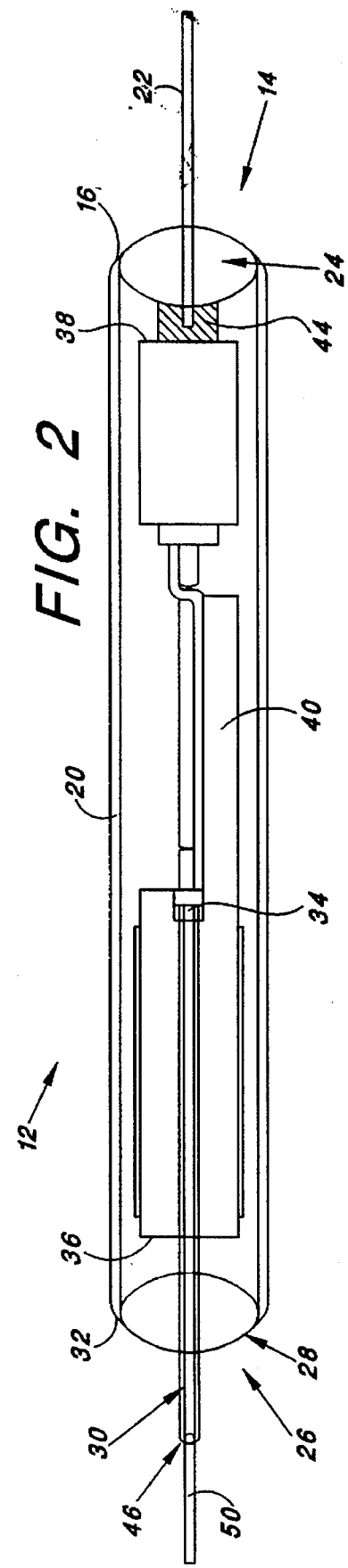

METHOD OF FORMING A TUBULAR FEED-THROUGH HERMETIC SEAL FOR AN IMPLANTABLE MEDICAL DEVICE

BACKGROUND OF THE INVENTION

The present invention relates to hermetically sealed cases or housings suitable for implantation within living tissue, and more particularly, to a method and apparatus for hermetically sealing an implantable device which prevents moisture from forming within the sealed device. In a preferred approach, the method and apparatus utilize a tubular feedthrough to vent moisture and other volatile gases trapped within the sealed device during the manufacturing process. Such tubular feedthrough also facilitates hermeticity testing of the implantable device during the manufacturing process.

Hermetically sealed cases or housings are widely used to protect electronic or other components that may be susceptible to damage or malfunction from exposure to the surrounding environment. The hermetic seal is simply an airtight, durable seal that is long-lasting and physically rugged. Sometimes the interior of an hermetically sealed enclosure is filled with an inert gas such as helium, to further retard the deterioration of the component or components inside. As no seal is perfect, the tightness of the hermetic seal, referred to as the hermeticity, is typically measured or specified in terms of the leakage rate through the seal, expressed in cc/sec of helium at standard temperature and pressure. Sometimes, for very low leakage rates, the hermeticity can only be measured by placing a radioactive gas within the enclosure and then using an appropriate radiation detector to "sniff" the seal for radioactive leaks.

Where the electrical component or components are to be implanted in body tissue, the hermetically sealed case (which must be made from a material that is compatible with body tissue, such as titanium, platinum or stainless steel or glass) serves a dual purpose: (1) it protects the electrical or other components housed in the device from body fluids and tissue, which fluids and tissue could otherwise prevent the components from performing their desired function; and (2) it protects the body tissue and fluids from the electrical or other components, which components may be made at least in part from materials that may be damaging to body tissue, and which therefore could pose a potential health risk to the patient wherein they are implanted. It is thus critically important that the hermetic seal of an implanted device be especially long-lasting and physically rugged. For this reason, stringent requirements are imposed on the hermeticity of an implanted device, typically requiring a seal that provides a helium leakage rate of less than $10^{-8}$ cc/sec at standard temperature and pressure (STP).

In recent years, the size of implanted medical devices has decreased dramatically. It is now possible, for example, to construct a simple stimulator device in a small hermetically sealed glass tube that can be implanted through the lumen of a needle. With such a small size comes increased requirements for the tightness of the hermetic seal because there is less empty space inside of the sealed unit to hold the moisture that eventually leaks therethrough. The hermeticity requirements of such small devices may thus be on the order of $10^{-11}$ or $10^{-12}$ cc/sec. While the small size is thus advantageous, the stringent hermeticity requirements imposed for such small devices makes them extremely difficult to manufacture, and thus increases the cost.

Most implanted medical devices, such as a cardiac pacemaker, neural stimulator, biochemical sensor, and the like, require hermetic conductive feedthroughs in order to establish electrical contact between the appropriate circuitry sealed in the hermetically closed case or capsule and an external electrode that must be in contact with the body tissue or fluids outside of the sealed case or capsule. In a pacemaker, for example, it is common to provide such a feedthrough by using a feedthrough capacitor. A representative feedthrough capacitor is described in U.S. Pat. No. 4,152,540. Alternatively, a hermetic feedthrough is typically used to establish electrical connections between the appropriate electronic components or circuitry sealed in the hermetically closed case or capsule and an external control device, or monitoring equipment.

Heretofore, an hermetic feedthrough for implantable devices has consisted of a ceramic or glass bead that is bonded chemically at its perimeter through brazing or the use of oxides, and/or mechanically bonded through compression, to the walls of the sealed case or capsule. A suitable wire or other conductor passes through the center of the bead, which wire or conductor must also be sealed to the bead through chemical bonds and/or mechanical compression. The feedthrough is thus circular, and the wire(s) or conductor(s) mounted within the bead are centered or mounted in a uniform pattern centrally positioned within the bead. Such centering is necessary due to the thermal coefficients required for the different expansion rates that occur when heat is applied to either create a compression seal or to create an oxide or bronze bond.

A significant problem associated with these hermetically sealed devices, particularly where the device is implanted in living tissue, is the inability to effectively seal the device with conventional feedthrough mechanisms. During existing sealing process, glass beads are fused within the device cases or capsules to hermetically seal the case or capsule. Water vapors are often produced by the gas flame fusing and are often trapped inside the capsules which water vapors may lead to eventual failure of the implanted device.

Another problem associate with conventional sealing processes is related to the expansion of gases remaining inside the sealed capsule. As the glass bead is fused to the case or capsule, air inside the case or capsule expands. The expanding air tries to escape from the case or capsule and is likely to result in localized stress in the glass fusion areas and may even form a hole through the molten glass. If a hole forms within the glass, it is very difficult if not impossible to repair.

Alternative methods of sealing microstimulator capsules involve expensive equipment such as an infrared laser or a dedicated glass diode sealing machine which utilizes heated formed graphic holding blocks.

Other examples of the related art pertaining to hermetic feedthrough assemblies for implantable medical devices are disclosed in U.S. Pat. No. 4,678,868 issued to Kraska et al., and U.S. Pat. No. 4,940,858 issued to Taylor et al. While these patents are directed to feedthrough assemblies for implanted medical devices, they do not address the problem of trapped water vapors and expanding air within the sealed device.

Still other art relating generally to methods for forming hermetically sealed cases having electrical feedthroughs and vias include U.S. Pat. No. 4,525,766 issued to Petersen, U.S. Pat. No. 4,861,641 issued to Foster et al., and U.S. Pat. No. 4,882,298 issued to Moeller et al. While these patents teach improvements in the art, such teachings are limited to use with semiconductor substrates and are not easily adaptable for use with microminiature devices implantable within living tissue.

It is thus evident that what is needed is a cost-effective manner of encapsulating implantable electronic or other devices that eliminates or prevents any moisture and expanding air from becoming trapped within the sealed device as the device is hermetically sealed. Further, once such device is sealed, there is a need for a cost-effective, non-destructive manner of testing the hermeticity of the sealed device during the manufacturing process.

SUMMARY OF THE INVENTION

The present invention addresses the above and other needs by providing a low cost method of encapsulating microstimulators and other implantable devices through the use of a tubular feedthrough. The tubular feedthrough allows moisture and expanding air trapped within the sealed device to vent during the manufacturing process. Further, the tubular feedthrough facilitates hermeticity testing at all stages of manufacturing by providing a channel through which a leakage testing apparatus may be attached to detect the presence of inert gases that are introduced in the environment surrounding the encapsulated device and that leak thereinto. Alternatively, an inert gas may be introduced into the capsule (encapsulated device) under pressure using the tubular feedthrough and thereafter the environment surrounding the capsule may be tested to see if any of the inert gas has leaked out from the capsule. Such leakage detection of the capsule can advantageously be accomplished via the tubular feedthrough at any time prior to sealing the feedthrough, or thereafter (in the case of inert gases being introduced into the capsule).

The present invention also permits electrical connection between electronic circuits sealed within the case or capsule and electrodes and/or other electrical terminals on the outside of the case or capsule. That is, while preventing moisture and expanding air from becoming trapped within the capsule as the assembly is sealed, as explained above, the tubular feedthrough may further provide a conductive path through the seal through which signal connections can be made. Alternative embodiments of the conductive tubular feedthrough contemplate more than just electrical conduction, but also include optical conduction, fluid conduction, etc., to allow signal connections between the interior and exterior of the hermetically sealed case or capsule.

BRIEF DESCRIPTION OF THE DRAWING

The above and other aspects, features and advantages of the present invention will be more apparent from the following more particular description thereof, presented in conjunction with the following drawings wherein:

FIG. 1 is a side, cross sectional view of a simple implantable device that is hermetically sealed in accordance with the present invention; and FIG. 2 is a side, cross sectional view of a microstimulator having the tubular feedthrough hermetic seal of the present invention.

DETAILED DESCRIPTION OF THE PREFERRED EMBODIMENT

Figure 3:
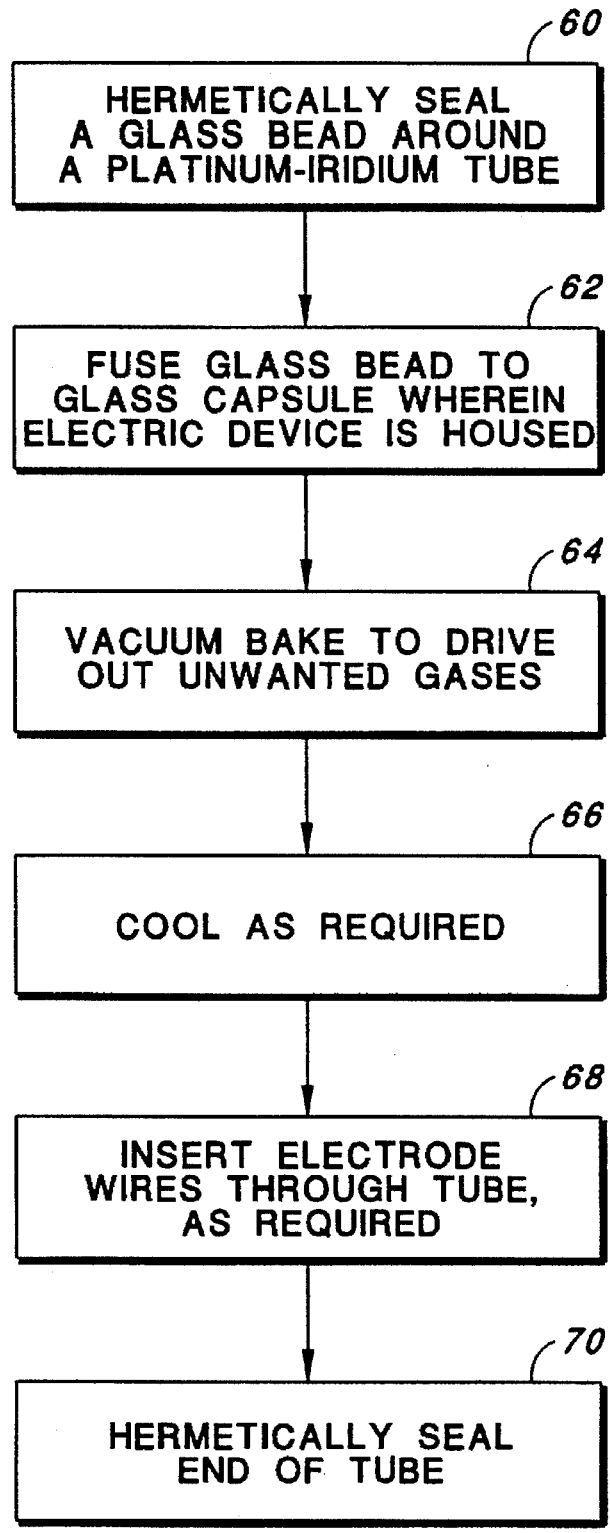
FIG. 3 is a flow diagram illustrating the method of the invention.

The following description is the best mode presently contemplated for carrying out the present invention. This description is not to be taken in a limiting sense, but is made merely for the purpose of describing the general principles of the invention. The scope of the invention should be determined with reference to the claims.

The tubular feedthrough disclosed herein is adapted for use with many different implantable electronic devices and particularly where it is advantageous to prevent entrapment of water vapors and other volatile gases within the sealed device. The disclosed method and apparatus is also adapted for use with hermetically sealed devices to allow hermeticity testing throughout the manufacturing process.

The preferred embodiment of the tubular feedthrough is particularly adapted for use with microstimulators, microtransducers, microtelemeters or similar electronic devices, or combinations of such devices. For example, the invention may be used with the microstimulator of the type disclosed in U.S. Pat. Nos. 5,193,539; and 5,193,540, incorporated herein by reference. Such microstimulators typically comprises: a capsule which is generally tubular glass capillary having two open ends; an electronic assembly; one or more hermetic seals and feedthroughs; and one or more active electrodes. It is to be understood, however, that the invention can be practiced with any type of implantable device wherein a hermetic seal is required, regardless of whether such device requires electronic circuitry or not.

Referring now to FIG. 1, there is shown a general representation of a simple implantable device 13 that is hermetically sealed in accordance with the methods described herein. The implantable device 13 includes a hermetically sealed casing 20, and a tube 30 that has one end 34 disposed within the casing 20 and the other end 35 extending out from the casing 20. The tube 30 is hermetically sealed to the casing 20 with the aid of a suitable seal 29 at the point of entry into the casing 20. In addition, an assembly 40, such as an electronic assembly, optical assembly or other component or element may be disposed within the casing 20 and connected to the tube 30 such that an appropriate connection between the encased assembly 40 and the outside of the casing 30 is established. A seal 49 is disposed in the end 35 of the tube 30 after any volatile gases within the casing 20 have been vented through the tube and after the implanted device 13 has been vacuum baked to drive out any moisture from the casing 20 through the tube 30. Such seal 49 may comprise a simple plug, or simply a crimp in the tube 30, or a weld, or any other means for hermetically closing the end 35 of the tube 30.

Prior to sealing the end 35 of the tube 30, hermeticity testing of the casing 20 can be easily accomplished in one of several manners. For example, by connecting a leakage detector 33 to the end 35 of the tube 30 extending from the casing 20 and introducing an inert detectable gas in the environment outside the sealed casing 20, one may find defective seals in the casing 20 by detecting the presence of the inert gas that leaks from the outside environment into the sealed casing 20. Alternatively, leaks may be detected by introducing an inert detectable gas into to the casing 20 via the tube 30 and subsequently detecting the presence of any inert detectable gas using the leakage detector 33 that leaks out of the casing 20.

Referring next to FIG. 2, the microstimulator 12 includes a first hermetic feedthrough conductor 14 that is formed at the aft end 16 of the glass capillary 20. The first feedthrough conductor 14 is preferably a metal wire 22 extending through a preformed glass bead 24. The preformed glass bead 24 is then placed within the aft end 16 of the glass capillary 20 and is hermetically sealed therein by fusing the aft end 16 of the glass capillary 20 with the glass bead 24 using a gas flame. A second feedthrough conductor 26 is formed by sealing a second glass bead 28 around a metal tubing 30. This second glass bead 28 is also dimensioned to snugly fit into the open forward end 32 of the glass capillary 20. The aft end 34 of the metal tubing 30 is then connected to the microstimulator electronic assembly 40 proximate the forward end 36 thereof.

The microstimulator electronic assembly 40 is then slid into the glass capillary 20. The radial dimension of the glass capillary 20 is such that the microstimulator electronic assembly 40 can be slid therein leaving a small clearance therebetween. The longitudinal dimensions of the microstimulator electronic assembly 40 and the glass capillary 20 are such that when the aft end 38 of the microstimulator electronic assembly 40 reaches the first conductive feedthrough 14, the open forward end 32 of the glass capillary 20 aligns with the second glass bead 28. A conductive epoxy connection 44 is made between the aft end 38 of the microstimulator electronic assembly 40 and the first hermetic feedthrough conductor 14.

Hermetic sealing of the forward end 32 of the glass capillary 20 is accomplished by fusing the forward end 32 of the glass capillary 20 with the second glass bead 28 using a gas flame. The metal tube 30 extending from the microstimulator electronic assembly 40 through the second glass bead 28 allows the expanded air and moisture to escape during the fusing process. After the glass bead to capillary sealing, the entire microstimulator 12 is vacuum baked until all the moisture and other volatile contaminates are driven out of the microstimulator capsule. If desired, an inert gas, such as helium or argon, may be pumped into the capsule. The forward end 46 of the metal tube 30 is then sealed or pinched off with a very small flame or some other sealing method such as a tungsten inert gas (TIG) flame, resistance welding, or laser welding. A microstimulator electrode wire 50 can be attached to the metal tube 30, as needed, during the pinching process or in a subsequently performed attachment step.

The method of forming a tubular feedthrough for an implanted electronic device in accordance with the present invention comprises three essential steps including: (a) attaching one end of a metal tube to an electronic assembly such that an electrical connection or feedthrough is established; (b) encasing the electronic assembly within a capsule such that one end of the metal tube resides in the interior of the sealed capsule while the other end extends out from of the capsule; and (c) hermetically sealing the metal tube to the capsule. The steps are performed in such a manner that the tubular feedthrough vents any moisture and other volatile gases that are trapped within the capsule and further allows hermeticity testing or leak detection of the sealed capsule. Changes in the order of the aforementioned steps may be made without sacrificing the advantages presented by this method.

A low cost method of hermetically sealing microstimulators, microtransducers, microtelemeters, and other implantable electronic devices such that moisture and expanding air trapped within the device are effectively vented, is illustrated in the flow diagram of FIG. 3. The method essentially comprises four steps. The first step (block 60 of FIG. 3) involves forming a venting feedthrough by having a glass bead hermetically sealed around a platinum-iridium tube. The platinum-iridium tube is preferably a small diameter tube on the order of about 0.25 mm outside diameter by 0.125 mm inside diameter by about 2.5 mm in length. One end of the platinum iridium tubing is attached to the forward end of the microstimulator electronic assembly forming an electrical connection therewith.

The second step involves fusing the glass bead to a suitable glass capsule such that the microstimulator electronic assembly is fully encased within the capsule (block 62 of FIG. 3). The glass bead and glass capsule are preferably dimensioned such that the glass bead snugly fits into the an open end of the glass capsule leaving little or no clearance therebetween. The glass-to-glass fusing is preferably/done using a gas-oxygen flame (or, as indicated below, an infrared laser) and is performed at a temperature of about 1180°–1200° C. (e.g., 1189° C.) being careful not to sustain heat damage to the microstimulator electronic assembly. During the glass fusing process, water vapors are produced by the gas-oxygen flame which heretofore would have been trapped inside the glass capsule. In addition, any air inside the capsule will expand due to the increased temperature. Advantageously, the platinum-iridium tube extending from the microstimulator electronic assembly through the glass bead, provides a path through which the expanded air and moisture are vented.

Alternatively, in lieu of using a gas-oxygen flame, an infrared laser could be used to seal the end of the tube. An infrared laser is particularly well suited for this operation because it may be used to melt the glass in an inert atmosphere, such as argon gas, and as a result no water is generated as the melting operation is performed. Hence, unlike the gas-oxygen flame, which produces water as one of its products, and which water could easily end up inside of the hermetic seal, the infrared laser (when used in an inert atmosphere) prevents the formation of water.

The third step in the described method for hermetically sealing microstimulators is vacuum baking of the entire microstimulator in an evacuated oven until all the moisture and other unwanted gases are driven out of the microstimulator capsule (block 64 of FIG. 3). The vacuum baking step is preferably performed at a temperature of about 80° C., for approximately 72 hours, again being careful not to damage the microstimulator electronic assembly.

Next, the microstimulator is cooled (block 66), and then the microstimulator electrode wires, or other wires needed for operation of the device, may then be inserted into the open end of the platinum-iridium tubing (block 68 of FIG. 3). The microstimulator electrode wires are also made from platinum-iridium and are dimension to fit within the platinum-iridium tube. The platinum-iridium electrode wire and platinum-iridium tube are then hermetically sealed (block 70 of FIG. 3) with a process such as resistance welding, a TIG flame, or laser welding. It should also be noted that the tube itself may be sealed without inserting an electrode wire therein, and the tube then functions (when properly electrically connected to the appropriate circuitry within the microstimulator) as the electrode wire. It is further noted that other dissimilar metals, which do not corrode, and which have an appropriate corresponding coefficient of expansion, may be used in lieu of platinum-iridium as the tube material.

Optionally, inert detectable gases, such as helium, may be introduced into the microstimulator capsule just prior to the final hermetic sealing. This additional step facilitates hermeticity testing at all subsequent stages of manufacturing. By detecting the presence of these inert gases outside the sealed capsule using various leakage tests, defective devices can be identified and receive the appropriate disposition.

From the foregoing, it should be appreciated that the present invention thus provides an improved method and apparatus for hermetically sealing microstimulators and other implantable electronic devices that prevents moisture and expanding air from becoming trapped within the sealed device. Further, it will be apparent that various changes and additions may be made in the described methods and in the form, construction and arrangement of the elements thereof without departing from the spirit and scope of the invention or sacrificing all of its material advantages, the forms and methods hereinbefore described being merely exemplary embodiments thereof. Therefore, it is not intended that the scope of the invention be limited to the specific embodiments and processes described. Rather, it is intended that the scope of this invention be determined by the appending claims and their equivalents.

What is claimed is:

1. A method of forming a hermetic seal for device to be implanted in living tissue, the device having a sealed casing, the method comprising the steps of:

inserting a tube into the device such that one end of a tube is disposed within the casing and the other end extends out from the casing;

hermetically sealing the tube to the casing;

venting any volatile gases within the casing through the tube;

vacuum baking the device to drive out any moisture from the casing through the tube; and sealing the end of the tube extending out from the casing.

2. The method of claim 1 further comprising the steps of:

connecting a leakage detector to the end of the tube extending from the casing prior to sealing the end of the tube;

introducing an inert detectable gas proximate to the sealed casing; and detecting the presence of any inert detectable gas that leaks into the sealed casing.

3. The method of claim 1 further comprising the steps of:

introducing an inert detectable gas into the casing via the tube and prior to sealing the end of the tube; and detecting the presence of any inert detectable gas that leaks out of the casing.

4. The method of claim 1 further comprising the steps of:

making the tube from an electrically conductive material;

placing an electronic assembly within the casing of the device; and connecting the one end of the tube disposed within the casing to the electronic assembly such that an electrical connection is established from the outside of the casing to the electronic assembly through the electrically conductive tube.

5. The method of claim 1 wherein the step of hermetically sealing the tube to the casing further comprises forming a glass bead around the tube and subsequently fusing the glass bead to the casing.

6. The method of claim 1 wherein the step of hermetically sealing the tube further comprises the steps of inserting wires into the open end of the tube and hermetically sealing the wires and tube together.

7. The method of claim 6 wherein the step of hermetically sealing the wires and tube together further comprises the step of welding the wires to the tube.

8. A method of hermetically sealing an electronic assembly within a capsule so that moisture and other unwanted gases are effectively vented from the capsule prior to sealing, the method comprising the steps of:

attaching one end of a tube to the electronic assembly;

encasing the electronic assembly within the capsule such that one end of the tube resides in the interior of the capsule while the other end extends out from the capsule;

hermetically sealing the tube to the capsule;

driving unwanted gases, including moisture if present, out of the capsule through the tube; and sealing the end of the tube extending out from the capsule.

9. The method of hermetically sealing as set forth in claim 8 wherein the step of driving moisture and other unwanted gases out of the capsule through the tube comprises elevating the temperature of the capsule for a prescribed period of time.

10. The method of hermetically sealing as set forth in claim 9 wherein the step of elevating the temperature of the capsule for a prescribed period of time comprises vacuum baking the capsule at a temperature of about 80 degrees C. for a time period of at least about 72 hours.

11. The method of hermetically sealing as set forth in claim 8 further including the step of inserting at least one wire connected to the electronic assembly through the tube.

12. The method of hermetically sealing as set forth in claim 8 wherein the tube comprises a metal tube, and further including the step of electrically connecting the metal tube to the electronic assembly, whereby electrical contact may be made with the electronic assembly from outside of the capsule by way of the metal tube.

13. The method of hermetically sealing as set forth in claim 8 further including introducing inert gases into the capsule through the tube immediately prior to sealing the end of the tube extending out from the capsule.

* * * * *